(12) United States Patent
Wang et al.

(10) Patent No.: US 10,073,042 B2
(45) Date of Patent: Sep. 11, 2018

(54) METHOD AND APPARATUS FOR IN-SITU FLUID EVALUATION

(71) Applicant: Schlumberger Technology Corporation, Sugar Land, TX (US)

(72) Inventors: Kang Wang, Beijing (CN); Younes Jalali, Shibuya-ku (JP); Yoko Morita, Hino (JP); Kamal Kader, Minato-Ku (JP); Yutaka Imasato, Chiba (JP)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 307 days.

(21) Appl. No.: 14/836,965

(22) Filed: Aug. 27, 2015

(65) Prior Publication Data

US 2016/0061743 A1   Mar. 3, 2016

Related U.S. Application Data

(60) Provisional application No. 62/043,415, filed on Aug. 29, 2014.

(51) Int. Cl.
*G01N 21/85* (2006.01)
*G01N 33/28* (2006.01)
*G01N 21/94* (2006.01)

(52) U.S. Cl.
CPC ..... *G01N 21/8507* (2013.01); *G01N 33/2823* (2013.01); *G01N 21/94* (2013.01); *G01N 2021/855* (2013.01)

(58) Field of Classification Search
CPC ............... G01N 21/8507; G01N 21/94; G01N 33/2823; G01N 2021/855
See application file for complete search history.

(56) References Cited

U.S. PATENT DOCUMENTS 5,939,717 A * 8/1999 Mullins ................ G01N 21/359
250/255
6,956,204 B2   10/2005 Dong et al.
(Continued)

FOREIGN PATENT DOCUMENTS

EP   1877646   6/2009

OTHER PUBLICATIONS

Hsu et al. "Multichannel oil-base mud contamination monitoring using downhole optical spectrometer", SPWLA 49th Annual Logging Symposium, May 25-28, 2008.*
(Continued)

*Primary Examiner* — Dominic J Bologna
(74) *Attorney, Agent, or Firm* — Sara K.M. Hinkley

(57) ABSTRACT

A method and apparatus are provided for performing in-situ fluid analysis. The method involves obtaining a first and second mixture of uncontaminated oil and a contaminant, wherein a percentage of the uncontaminated oil in the first mixture is different from the second mixture. The method may further include establishing a rate of change of a physical property of the first mixture and the second mixture to estimate a mass density of the uncontaminated oil and a mass density of the contaminant. In addition, the method may include obtaining a volume fraction of the uncontaminated oil for the first mixture and second mixture using the mass density of the uncontaminated oil and the mass density of the contaminant. An optical device may be used to determine a composition of the first and second mixtures in order to calculate a composition of the contaminant and a composition of the uncontaminated oil.

16 Claims, 10 Drawing Sheets

(56) References Cited

U.S. PATENT DOCUMENTS

| | | |
|---|---|---|
| 7,458,252 B2 | 12/2008 | Freemark et al. |
| 8,024,125 B2 | 9/2011 | Hsu et al. |
| 2003/0229448 A1* | 12/2003 | Storm, Jr. .......... G01N 33/2823 702/6 |
| 2005/0182566 A1* | 8/2005 | DiFoggio ................ E21B 47/10 702/11 |
| 2007/0079962 A1* | 4/2007 | Zazovsky ............. E21B 49/008 166/264 |
| 2009/0150079 A1* | 6/2009 | Hsu ........................ E21B 49/10 702/11 |
| 2014/0180591 A1 | 6/2014 | Hsu et al. |
| 2014/0193153 A1 | 7/2014 | Hosoda |
| 2014/0239168 A1 | 8/2014 | Wang et al. |
| 2014/0240862 A1 | 8/2014 | Kamiya et al. |
| 2014/0316705 A1 | 10/2014 | Zuo et al. |
| 2014/0352397 A1 | 12/2014 | Smits |
| 2015/0066458 A1 | 3/2015 | Coles et al. |
| 2015/0142317 A1 | 5/2015 | Zuo et al. |

OTHER PUBLICATIONS

International search report and written opinion for the equivalent PCT patent application No. PCT/IB2015/001460 dated Jan. 11, 2016.

International Preliminary Report on Patentability issued in the related PCT application PCT/IB2015/001460, dated Feb. 28, 2017 (11 pages).

* cited by examiner

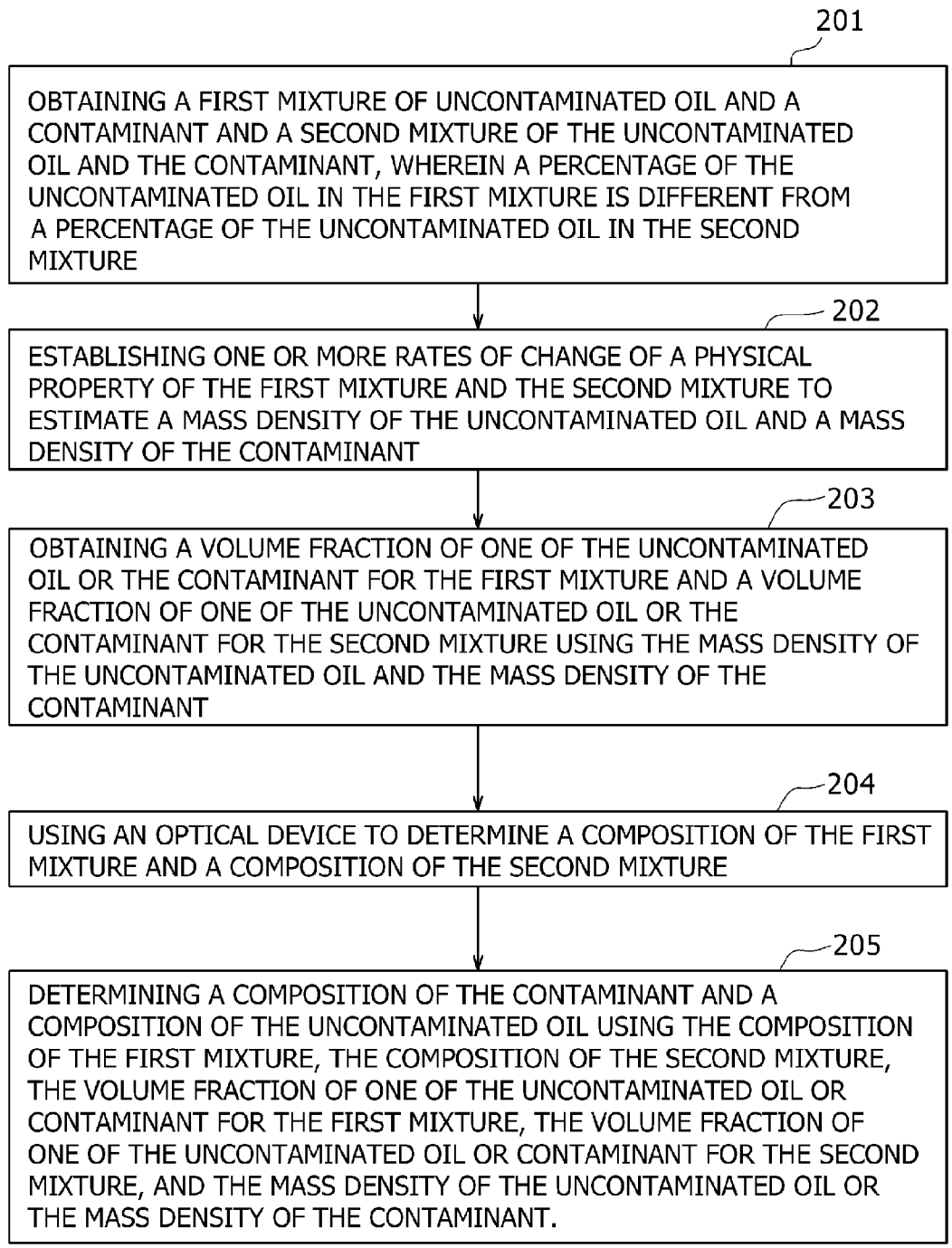

FIG. 3B

301 — OBTAINING A FIRST MIXTURE OF UNCONTAMINATED OIL AND A CONTAMINANT AND A SECOND MIXTURE OF THE UNCONTAMINATED OIL AND THE CONTAMINANT, WHEREIN A PERCENTAGE OF THE UNCONTAMINATED OIL IN THE FIRST MIXTURE IS DIFFERENT FROM A PERCENTAGE OF THE UNCONTAMINATED OIL IN THE SECOND MIXTURE

↓

302 — ESTABLISHING A RATE OF CHANGE OF GAS-OIL-RATIO VERSUS MASS DENSITY OF THE FIRST MIXTURE AND THE SECOND MIXTURE

↓

303 — ESTIMATING A MASS DENSITY OF THE CONTAMINANT

↓

304 — ESTABLISHING AN ASYMPTOTIC LIMIT OF OPTICAL DENSITY VERSUS PUMP OUT FOR THE FIRST MIXTURE AND THE SECOND MIXTURE

↓

305 — ESTABLISHING RATE OF CHANGE OF THE OPTICAL DENSITY VERSUS THE MASS DENSITY FOR THE FIRST MIXTURE AND THE SECOND MIXTURE

↓

306 — ESTIMATING A MASS DENSITY OF THE UNCONTAMINATED OIL

↓

307 — OBTAINING A VOLUME FRACTION OF ONE OF THE UNCONTAMINATED OIL OR THE CONTAMINANT FOR THE FIRST MIXTURE AND A VOLUME FRACTION OF ONE OF THE UNCONTAMINATED OIL OR THE CONTAMINANT FOR THE SECOND MIXTURE USING THE DENSITY OF THE UNCONTAMINATED OIL AND THE CONTAMINANT

↓

308 — USING AN OPTICAL DEVICE TO DETERMINE A COMPOSITION OF THE FIRST MIXTURE AND A COMPOSITION OF THE SECOND MIXTURE

↓

309 — CONVERTING THE VOLUME FRACTION OF THE ONE OF THE UNCONTAMINATED OIL OR THE CONTAMINANT FOR THE FIRST MIXTURE AND THE VOLUME FRACTION OF THE ONE OF THE UNCONTAMINATED OIL OR THE CONTAMINANT FOR THE SECOND MIXTURE INTO A WEIGHT FRACTION OF THE FIRST MIXTURE AND A WEIGHT FRACTION OF THE SECOND MIXTURE

↓

310 — DETERMINING A COMPOSITION OF THE UNCONTAMINATED OIL AND A COMPOSITION OF THE CONTAMINANT USING THE COMPOSITION OF THE FIRST MIXTURE, THE COMPOSITION OF THE SECOND MIXTURE, THE WEIGHT FRACTION OF THE FIRST MIXTURE AND THE WEIGHT FRACTION OF THE SECOND MIXTURE.

METHOD AND APPARATUS FOR IN-SITU FLUID EVALUATION

CROSS-REFERENCE TO RELATED APPLICATION

The present document is based on and claims priority to U.S. Provisional Application Ser. No. 62/043,415, "Method and Apparatus for Downhole Sampling Estimation", filed Aug. 29, 2014, the contents of which are incorporated herein by reference for all intents and purposes.

BACKGROUND

This section is intended to introduce various ideas of art that may be related to portions of the present techniques, which are described and/or claimed below. This discussion is believed to be helpful in providing background information to facilitate a better understanding of the various embodiments of the present disclosure. Accordingly, it should be understood that these statements are to be read in this light, and not as admissions of prior art.

This disclosure relates generally to methods and apparatus for Downhole Fluid Analysis (DFA). DFA is used to provide information in-situ about the properties of subterranean formations and/or the compositions of reservoir fluids, while the tool is still deployed. Such information can be used to improve or optimize the effectiveness of formation testing tool operations during various sampling processes in a given well, including sampling processes which monitor the effluent from the formation but don't necessarily return a captured formation fluid sample to the Earth's surface. The use of DFA allows for reducing and/or optimizing the number of samples captured and brought back to the surface for further detailed analysis. In addition, DFA can also provide real time information on the status of cleaning operations for a wellbore, among other uses.

Contaminants are often introduced into a well as a result of a drilling process. For example, to facilitate drilling a drilling mud is introduced into the well as a lubricant to reduce the effects of friction between a drill bit and the formation. Consequently, contamination of formation fluid may occur when a filtrate of the drilling mud permeates the formation walls during and after drilling. When drawing formation fluid samples in order to measure the formation fluid quality, the formation fluid samples will often contain a mixture of formation fluid and this mud filtrate. The amount of mud filtrate in a formation fluid sample contaminates the formation fluid and makes it difficult to accurately or precisely determine formation fluid (or hydrocarbon, oil, etc.) composition.

As will become apparent from the following description and discussion, the present disclosure provides methods and apparatus for estimating formation fluid composition that is capable of operating in downhole applications.

SUMMARY OF THE DISCLOSURE

This summary is provided to introduce a selection of concepts that are further described below in the detailed description. This summary is not intended to identify any key or essential features of the claimed subject matter, nor is it intended to be used as an aid in limiting the scope of the claimed subject matter.

In at least one embodiment of the present disclosure, a method is provided for analyzing well properties in-situ, comprising obtaining a first mixture of uncontaminated oil and a contaminant and a second mixture of the uncontaminated oil and the contaminant, wherein a percentage of the uncontaminated oil in the first mixture is different from a percentage of the uncontaminated oil in the second mixture. The method may further comprise establishing one or more rates of change of a physical property of the first mixture and the second mixture to estimate a mass density of the uncontaminated oil and a mass density of the contaminant and obtaining a volume fraction of one of the uncontaminated oil or the contaminant for the first mixture and a volume fraction of one of the uncontaminated oil or the contaminant for the second mixture using the mass density of the uncontaminated oil and the mass density of the contaminant.

In some embodiments, the method may further comprise using an optical device to determine a composition of the first mixture and a composition of the second mixture and determining a composition of the contaminant and a composition of the uncontaminated oil using the composition of the first mixture, the composition of the second mixture, the volume fraction of one of the uncontaminated oil or contaminant for the first mixture, the volume fraction of one of the uncontaminated oil or contaminant for the second mixture, and the mass density of the uncontaminated oil or the mass density of the contaminant.

While still further embodiments may provide a downhole fluid analyzer including a probe having one or more flow lines and an optical device for determining a first optical density of a first mixture of uncontaminated oil and contaminant and a second optical density of a second mixture of the uncontaminated oil and the contaminant and for determining a composition of the first mixture and a composition of the second mixture. The downhole fluid analyzer may further include a densitometer for determining a first density of the first mixture and a second density of the second mixture and a processor to estimate a density of the contaminant and to estimate a density of the uncontaminated oil. Wherein the processor determines a volume fraction of one of the uncontaminated oil or contaminant for the first mixture and a volume fraction of one of the uncontaminated oil or contaminant for the second mixture.

Advantages and novel features of the disclosures will be set forth in the description which follows or may be learned by those skilled in the art through reading the materials herein.

BRIEF DESCRIPTION OF THE DRAWINGS

Embodiments of methods and apparatus for downhole sampling estimation according to the disclosures herein are described with reference to the following figures. The same numbers are used throughout the figures to reference like features and components.

FIG. 2 depicts a flowchart of an estimation of composition of uncontaminated oil and contaminant in accordance with an embodiment of the present disclosure;

FIG. 3B depicts a flowchart of an estimation of composition of uncontaminated oil and contaminant in accordance with an embodiment of the present disclosure;

FIGS. 8A, 8B-7.2 show exemplary plots of uncontaminated oil composition and contaminate composition (respectively) versus pump out volume in accordance with an embodiment of the present disclosure;

DETAILED DESCRIPTION

Illustrative embodiments and aspects of the present disclosure are described below. In the interest of clarity, not all features of an actual implementation are described in the specification. It will of course be appreciated that in the development of any such actual embodiment, numerous implementation-specific decisions must be made in order to achieve the developers' specific goals, such as compliance with system-related and business-related constraints, which will vary from one implementation to another. Moreover, it will be appreciated that such development effort might be complex and time-consuming, but would nevertheless be a routine undertaking for those of ordinary skill in the art having benefit of the disclosure herein.

The present disclosure relates to formation evaluation involving fluid analysis. In particular, the present disclosure describes systems, apparatuses and methods for performing downhole fluid analysis and/or utilizing a fluid analyzer. A fluid analyzer is position-able in a downhole tool and deployable into a wellbore for analyzing fluid drawn into the fluid analyzer in the downhole tool.

'Formation evaluation' as used herein generally relates to the measurement, testing, sampling, and/or other analysis of wellsite materials, such as gases, fluids and/or solids. Such formation evaluation may be performed at a downhole location (in-situ) to provide data associated with the formation. Examples of such data obtained may include downhole parameters (e.g., temperature, pressure, permeability, porosity, etc.), material properties (e.g., viscosity, composition, density, etc.), and the like.

'Fluid analysis' as used herein generally relates to a type of formation evaluation of downhole fluids, such as wellbore, formation, reservoir, and/or other fluids located at a wellsite. Fluid analysis may be performed by a fluid analyzer capable of measuring fluid properties, such as viscosity, composition, density, temperature, pressure, flow rate, optical parameters, etc. Fluid analysis may be performed using, for example, optical sensors (e.g., spectrometers), gauges (e.g., quartz), densitometers, viscometers, resistivity sensors, nuclear sensors, and/or other fluid measurement and/or detection devices among others.

'Oil' as used herein generally refers to any hydrocarbon in any form, such as liquid or gas for example. 'Contaminant' as used herein may generally refer to a filtrate or a fluid separated from oil-based mud (OBM) or water-based mud (WBM). 'Uncontaminated oil' as used herein generally refers to a hydrocarbon that is sufficiently pure, pristine, uncontaminated or otherwise considered in the fluid sampling and analysis field to be an acceptable representative of a given formation for valid hydrocarbon sampling and/or evaluation. Persons of skill in the art recognize that uncontaminated oil may be less than 100% pure and may contain an acceptable level of contaminants while still resulting in a valid and representative sample.

Figure 1A:
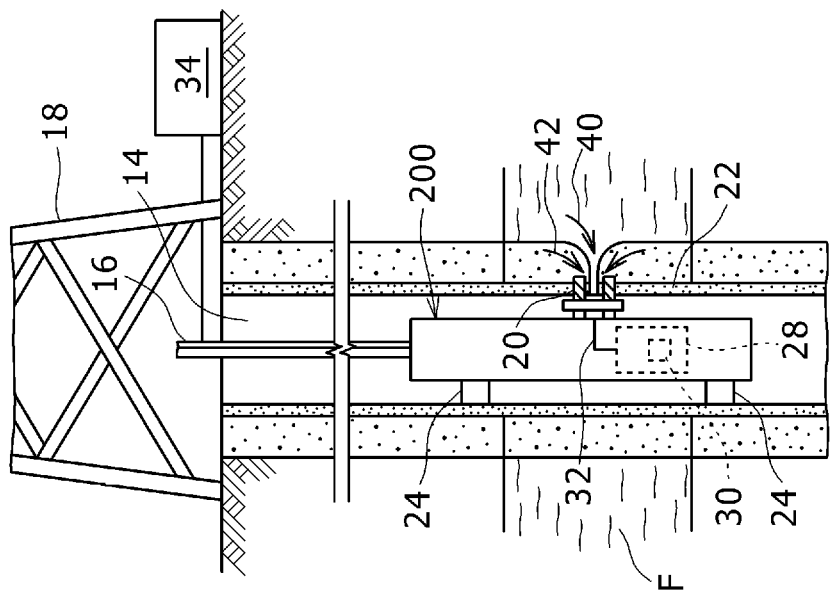
FIGS. 1A and 1B depict schematic views, partially in cross-section, of a wellsite with a downhole drilling tool and a downhole wireline tool, respectively, deployed into a wellbore for performing downhole formation evaluation in accordance with embodiments of the present disclosure.
Figure 1B:
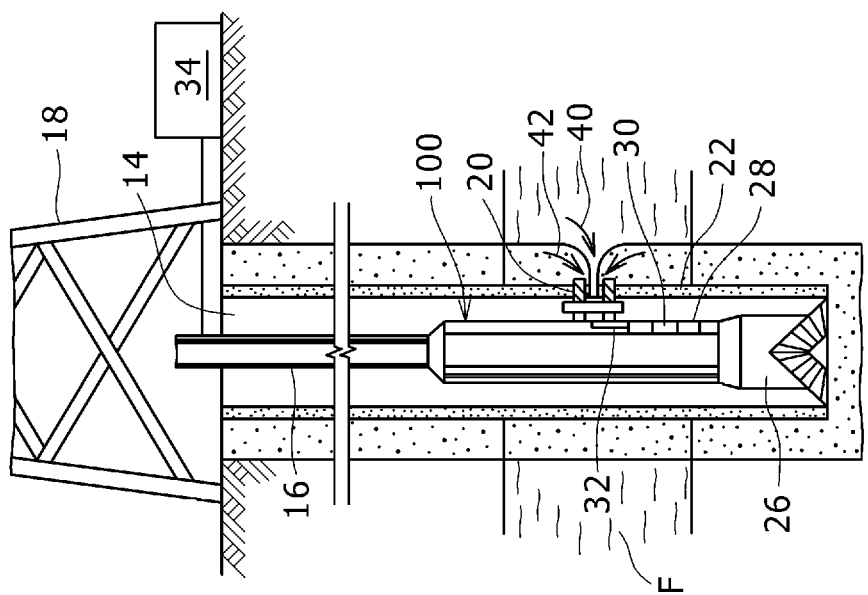

Referring now to exemplary FIGS. 1A and 1B that generally depict environments in which the subject matter of the present disclosure may be implemented. FIG. 1A depicts a downhole drilling tool 100 and FIG. 1B depicts a downhole wireline tool 200, either of which may be used for performing formation evaluation in accordance with embodiments of the present disclosure as well as other tools not specifically identified. As will be appreciated by a person skill in the art, any form of conveyance for a formation evaluation tool may be considered and used along with embodiments of this disclosure, and are not limited to the two types shown in these exemplary reference figures.

With regards to FIG. 1A, the downhole drilling tool 100 may be advanced into a subterranean formation F to form a wellbore 14. The downhole drilling tool 100 may be conveyed alone or along with one or more measurement-while-drilling (MWD) tools, logging-while-drilling (LWD) tools, or other drilling tools and drill bits. The downhole drilling tool 100 may be attached to a conveyance 16 (e.g., such as drill string in this case) and driven by a rig 18 to form the wellbore 14.

In some embodiments, the downhole drilling tool 100 may include a probe 20 adapted to couple with a wall 22 of the wellbore 14 in order to draw mixtures of fluid from the formation F into the downhole drilling tool 100. Since the downhole drilling tool 100 is constantly rotating while forming the wellbore 14, the probe 20 may extend from an interior portion of the downhole drilling tool 100, or otherwise be protected from the harsh environment of the drilling fluid, rotation, and abrasion from the walls 22 of the wellbore 14.

The fluid from the formation F may include uncontaminated oil 40 and a contaminant 42. The arrows shown in relation to the uncontaminated oil 40 and the contaminant 42 indicate the flow direction of fluid during sampling. As the drill bit 26 of drilling tool 100 progresses, a contaminant such as mud filtrate from the Oil-based mud (OBM) may be formed or left on the walls 22 of wellbore 14. As the filtrate leaches into the surrounding formation, a contaminated zone may form to surround the walls 22 of wellbore 14 and is indicated by the area identified with the contaminate 42.

In other embodiments, a downhole wireline tool 200 of FIG. 1B may be deployed from the rig 18 into the wellbore 14 via a conveyance 16 (e.g., such as a wireline cable in this case). Although a rig 18 is shown, deployment of the wireline cable is not limited to this device and the rig 18 is merely shown for simplicity in description. As stated earlier, the particular type of conveyance and technique or equipment used for deployment may be selected from among those known to people of average skill in the art.

The downhole wireline tool 200 may also be provided with a probe 20 adapted to couple with the wall 22 of the wellbore 14 and draw mixtures of fluid from the formation F into the downhole wireline tool 200. However, unlike the downhole drilling tool 100, the probe 20 of downhole wireline tool 200 may not require the same level of protection or configuration for wireline deployment. As shown in the exemplary figure, the probe 20 may extend partially away from the downhole wireline tool 200, either retractably from within an interior cavity or the surface of the tool.

Pistons 24 may be used to assist in urging and/or directing the downhole wireline tool 200 and probe 20 against the wellbore wall 22 and adjacent the formation F, thereby fluidly coupling the probe 20 to the formation F. Of course, in some cases the probe 20 may extend out in conjunction with or separately from with the pistons 24 in order to contact the wall 22 of wellbore 14.

As shown in FIGS. 1A and 1B, in some embodiments the downhole drilling tool 100 and the downhole wireline tool 200 may also be provided with a formation evaluation tool 28. The formation evaluation tool may comprise a fluid analyzer 30 for analyzing any mixtures of downhole fluid drawn into the respective probes 20 of the downhole tools 100 and 200. The formation evaluation tool 28 may also include at least one flow line 32 for receiving mixtures of the downhole fluid. The downhole fluid may comprise mixtures of uncontaminated oil 40 and contaminant 42 from the probe 20. Flow line 32 may pass the mixtures of downhole fluid to the fluid analyzer 30 for analysis, as will be described more fully herein. Further embodiments may include a surface unit 34 that is provided to be communicatively coupled with the downhole tools 100, 200 and transfer of signals (e.g., data, power, command, etc.) there between.

Referring generally now to exemplary FIG. 2, a flowchart is presented that represents an embodiment of a method used in-situ to determine the amount of contaminant in the wellbore 14 and to enable the determination of a composition of uncontaminated oil. Initially, as shown in block 201, the flowchart describes obtaining mixtures of downhole fluid. A first mixture of the uncontaminated oil and a contaminant and a second mixture of the uncontaminated oil and the contaminant are obtained wherein a percentage of the uncontaminated oil in the first mixture is different from a percentage of the uncontaminated oil in the second mixture.

Obtaining of the two mixtures of downhole fluid may be accomplished in a number of ways. In some embodiments the first and the second mixtures can be sampled by a single flow line at different points in time, in some cases such as while a wellbore cleaning operation is occurring over time. Alternatively, the first mixture can be sampled by one flow line at one time, and the second mixture can be sampled by another flow line at the same or a different time. If different times are used, a time interval may be selected that corresponds to the clean-up process in order to differentiate the two mixtures. For example, during clean-up there may be decreasing levels of mass density if normal oil (i.e. not heavy oil) is being sampled, as well as increasing measurements of optical density as the percentage of uncontaminated oil increases. In addition, increasing levels of the gas-oil ratio may further indicate an increasing percentage of uncontaminated oil, since in many cases the uncontaminated oil will contain a substantially less dense gas phase as opposed to the higher density (in some cases, degassed) filtrate or contaminant component.

Accordingly, two mixtures of different levels of uncontaminated oil and contaminate may be obtained. Increases in the difference between the percentages of uncontaminated oil in each mixture can allow for increases in the accuracy of the estimations that are performed later in the method. However, there is no requirement that the difference be above a certain threshold for the embodiments of this disclosure to work, just that the percentages of the amounts of uncontaminated oil in each mixture be different.

As generally shown in block 202, some embodiments comprise establishing a rate of change of a physical property of the first mixture and a rate of change of a physical property of the second mixture. Physical properties may include, but not be limited to, Gas-Oil-Ratio (GOR), Optical Density (OD), and mass density, among others. For example, the mass density of the first mixture and the mass density of the second mixture can be measured and a time rate tendency for the mass densities with respect to pumping volume or GOR can be established.

For some embodiments, the mass density measurement data may be obtained with a densitometer, or other methods known to those of skill in the art. Since mass density obeys a well-established mixing rule (as long as the two fluids being mixed do not exhibit appreciable non-additive volume behavior), the mass density of the mixture of two fluids (in which each fluid has a different density) can be correlated to a measure of the volume fraction of the two components present.

As generally described in block 203, the mass density of the first mixture and the mas density of the second mixture are determined in order to estimate the mass density of the contaminant and the mass density of the uncontaminated oil. As described earlier, the mass density of the first and second mixture may be measured using a densitometer in some embodiments. Using the mixing rule, the density of each mixture is related to the proportional amounts of the mass density of the contaminant and the mass density of the uncontaminated oil in each of the mixtures. This results in four unknowns and two equations, Eq. 1 and Eq. 2.

$$D1_{mixture1} = V1_{uncontaminatedoil} * D_{uncontaminatedoil} + (1 - V1_{uncontaminatedoil}) * D_{contaminant} \quad \text{(Eq. 1)}$$

$$D2_{mixture2} = V2_{uncontaminatedoil} * D_{uncontaminatedoil} + (1 - V2_{uncontaminatedoil}) * D_{contaminant} \quad \text{(Eq. 2)}$$

Where $D1_{mixture\ 1}$ and $D2_{mixture\ 2}$ are measured mass density values from the densitometer. $D_{uncontaminated\ oil}$ is the unknown mass density for uncontaminated oil and $D_{contaminant}$ is the unknown mass density for the contaminant. $V1_{uncontaminated\ oil}$ is the unknown volume fraction of uncontaminated oil in mixture 1 and $V2_{uncontaminated\ oil}$ is the unknown volume fraction of uncontaminated oil in mixture 2. Although the equations are shown using the volume fraction for uncontaminated oil, the equations could easily be written to reflect the volume fraction for contaminant. The volume fraction for uncontaminated oil is the volume of uncontaminated oil divided by the sum of the volume of uncontaminated oil and the volume of contaminant.

Figure 4:
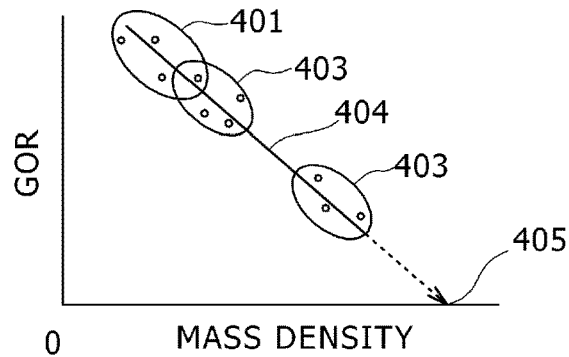
FIG. 4 shows an exemplary rate of change in gas-oil ratio (GOR) versus mass density in order to facilitate estimation of the mass density of the contaminant in accordance with an embodiment of the present disclosure.

The density of the contaminant $D_{contaminant}$ can be determined based in part on referring to a graph of GOR vs. Mass Density as shown in FIG. 4. As generally shown in the figure, various values of $D1_{mixture\ 1}$ and $D2_{mixture\ 2}$ are plotted in the GOR vs. Mass Density Graph. Data clusters 401, 402, and 403 refer to three exemplary sets of mass densities of mixtures. For example, data cluster 401 may represent measured mass density data of a first mixture and data cluster 402 may represent measured mass density data of a second mixture in which both mixtures were obtained from one flow line at different points in time. Data cluster 404 may represent measured mass density data of a second mixture obtained from another flow line, or a mass density of a third or more mixture. Alternatively, a single data cluster, such as 402 for example, may be used with points spreading across different times.

With a single mixture across a period of time or two or more mixtures at different locations, a data trend may be observed and fitted by a linear best fit line 404, for example. In this case, the result is shown as a linear trend, but the best fit line may not be limited to this example. As stated earlier, the wider the spread of data points and the increasing number of data points results in increasing levels of accuracy and precision for the linear best fit curve 404.

Using FIG. 4 and an assumption that as the contaminant becomes more pure (i.e., without mixtures of uncontaminated oil), the GOR should decrease to approximately zero. This is due to an assumption that pure uncontaminated oil should contain some amount of gas phases and that pure contaminant will be substantially degassed. Accordingly, the mass density of the pure contaminant can be estimated by extrapolating the linear trend of best fit line 404 in this example to the assumed case of approximately zero gas-oil-ratio, as indicated by the mass density value 405. With the determination of the mass density of the contaminant, there are only three unknowns for the two previous equations.

Figure 5:
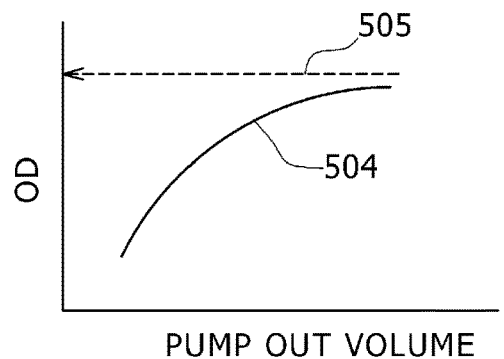
FIG. 5 shows an exemplary rate of change in optical density (OD) versus pump out volume in order to facilitate the estimation of the optical density of the uncontaminated oil in accordance with an embodiment of the present disclosure.

Referring generally now to FIG. 5, this exemplary graph shows a plot of optical density (OD) versus pump out volume. The graph may be constructed using data from the two or more mixtures similar to way FIG. 4 was described. Generally, OD measurement data can be generated using a plurality of wavelengths. The OD of the mixtures is determined with an optical device such as an optical spectrometer, and the results plotted versus pump out volume. As shown in the figure, the best fit curve 504 (e.g., such as a second order line) may be obtained from OD measurement data of the first and the second mixtures. During a well clean out operation or with continued pumping, the mixture compositions will begin to have higher compositions of uncontaminated oil relative to contaminant. Uncontaminated oil is assumed to have the highest level of optical absorption, so that when the optical density reaches a plateau, the resulting horizontal asymptote for the graph should correlate to the OD of pure uncontaminated oil. This $OD_{uncontaminated\ oil}$ 505 represented by the horizontal asymptote can be assumed to be an estimate of the OD of pure uncontaminated oil.

Figure 6:
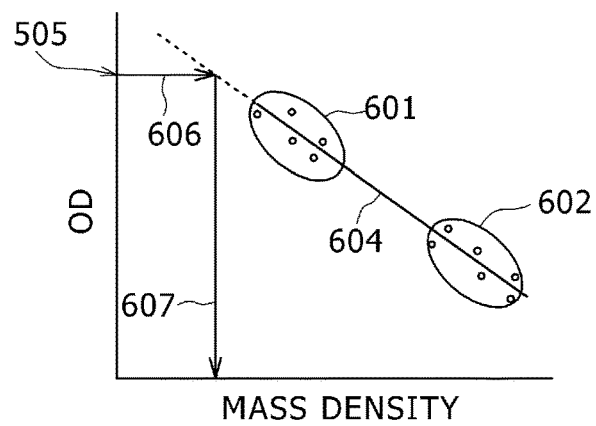
FIG. 6 shows an exemplary rate of change in OD versus mass density in order to facilitate the estimation of the mass density of the uncontaminated oil from the optical density of the uncontaminated oil in accordance with an embodiment of the present disclosure.

Since the mass density of the uncontaminated oil is still unknown, another graph, in this case represented by exemplary FIG. 6 showing OD versus Mass Density, can be generated. As with the previous graphs, the data clusters 601 and 602 can represent a variety of configurations composed of first and second mixtures obtained in numerous ways. Although there has been different data clusters shown in these exemplary graphs, all of the data used to generate the graphs is obtained from the same mixtures of downhole fluid. For FIG. 6, the data clusters 601 and 602 are approximated with a linear best fit line 604 in order to show the trend for the data. Once this figure is established, OD can be converted into Mass Density.

The OD of the pure uncontaminated oil is represented by horizontal line 606 based on the value $OD_{uncontaminated\ oil}$ 505. The OD of the pure uncontaminated oil can be converted into the mass density of pure uncontaminated oil by determining the intersection of horizontal line 606 with linear best fit line 604. The intersection represents the $D_{uncontaminated\ oil}$ 607.

With $D_{uncontaminated\ oil}$ 607, the only remaining unknowns from Eq. 1 and Eq. 2 are the relative volume fractions of uncontaminated oil and contaminate in the first mixture and the second mixture. As stated in block 203, the $D_{uncontaminated\ oil}$ and the $D_{contaminant}$ can be used to estimate the volume fractions $V1_{uncontaminated\ oil}$ and $V2_{uncontaminated\ oil}$ using Eq. 1 and Eq. 2. Since there are two equations and two unknowns, the relative volume fractions can be solved for one another as long as the volume fractions of uncontaminated oil (for example) for the first and second mixtures are not identical, and they should not be identical if the mass density of mixture 1 is different than the mass density of mixture 2. In some cases, the uncertainty in the density of the uncontaminated oil and the contaminant may be estimated by repeating the blocks 201-203 listed in the flow chart.

Figure 7:
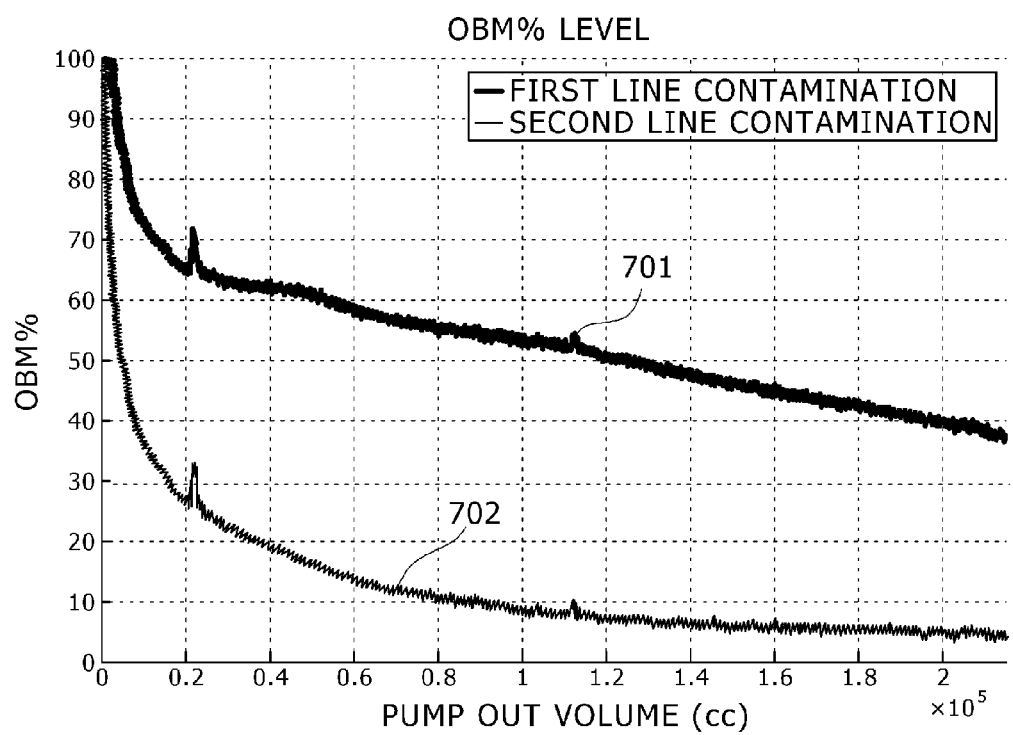
FIG. 7 shows an exemplary rate of change in Oil Based Mud percentage (OBM %) versus pump out volume in order to visualize the status of a cleanup operation for a wellbore in accordance with an embodiment of the present disclosure.

Turning briefly to exemplary FIG. 7, this figure generally shows the trends of oil based mud (OBM) percentage (i.e., represented here on the vertical axis) (e.g., OBM is a common contaminant) during a well bore cleaning operation. The OBM percentage, which can be referred to in terms of volume fraction or weight fraction, is shown to decrease (i.e., representing a reduction in the contamination level of mud filtrate as the cleaning operation progresses. Both lines in the figure represent the same general rate of reduction of contaminant in the well bore.

In the exemplary embodiment shown, the first line 701 (top curve) may be from one flow line and the second line 702 (bottom curve), may be from another flow line. The graph is representative of an embodiment of a concentric configuration of flow lines where the first line 701 may be an outer flow line more exposed to contaminant and the second line 702 may be an inner flow line able to obtain less contaminated samples. The general configuration of concentric flow lines will be discussed later. The outer flow line in the embodiment may be referred to as a guard line, since the outer concentric flow line removes a majority of contaminant and protects or guards the interior concentric line from being significantly exposed to the contaminant after a period of pump out. The inner concentric flow line may be referred to as a sample line, since in some applications the inner concentric flow line may also be used for obtaining samples to be brought to the surface for additional analysis or consideration.

By determining the volume fractions of the uncontaminated oil and the contaminant in-situ during a well bore cleaning operation, an operator may be able to gauge the progress and effectiveness of the cleaning operation. In addition, if samples are obtained from the flow line resulting in the second line 702, an operator may also be able to determine when the timing is appropriate to take a sample from the flow line resulting in the second line 702. In both cases, an operator may be able to reduce the time spend during a well bore cleaning operation or a sampling operation, saving money and rig time in the process.

Returning to FIG. 2, as shown in exemplary block 204, an optical device may be used to determine the composition of the first mixture and composition of the second mixture (e.g., $C1_{mixture\ 1}$, and $C2_{mixture\ 2}$ of Eqs. 3 and 4). In some embodiments, the optical device may comprise a compositional fluid analyzer (CFA) or spectrometer 60 (see FIGS. 9A and 9B). The compositions of uncontaminated oil and contaminant comprise C1, C2, C3, C4, C5 and C6+. C1 refers to methane, C2 refers to ethane, C3-C5 refer to propane, butane, and pentane, and C6+ are other components.

Referring generally now to block 205, and using Eqs. 3 and 4 below, the composition of the contaminant and the composition of the uncontaminated oil can be determined using $C1_{mixture\ 1}$ and $C2_{mixture\ 2}$, the measured compositions of mixture 1 and mixture 2, $VF1_{uncontaminated\ oil}$ and $VF2_{uncontaminated\ oil}$, the calculated volume fraction of uncontaminated oil for mixture 1 and mixture 2, $D_{uncontaminated\ oil}$, the density of uncontaminated oil, and $D_{contaminant}$, the density of contaminant. Even though Eqs. 3 and 4 are repeated below using volume fraction terms, it is well within the scope of this disclosure to write the equations in terms of weight fractions instead of volume fractions and densities.

$$C1_{mixture1} = (VF1_{uncontaminatedoil} * D_{uncontaminatedoil} / (VF1_{uncontaminatedoil} * D_{uncontaminatedoil} + (1 - VF1_{uncontaminatedoil}) * D_{contaminant})) * C_{uncontaminatedoil} + ((1 - VF1_{uncontaminatedoil}) * D_{contaminantoil} / (VF1_{uncontaminatedoil} * D_{uncontaminatedoil} + (1 - VF1_{uncontaminatedoil}) * D_{contaminant})) * C_{contaminant} \quad \text{(Eq. 3)}$$

$$C2_{mixture2} = (VF2_{uncontaminatedoil} * D_{uncontaminatedoil} / (VF2_{uncontaminatedoil} * D_{uncontaminatedoil} + (1 - VF2_{uncontaminatedoil}) * D_{contaminant})) * C_{uncontaminatedoil} + ((1 - VF2_{uncontaminatedoil}) * D_{contaminantoil} / (VF2_{uncontaminatedoil} * D_{uncontaminatedoil} + (1 - VF2_{uncontaminatedoil}) * D_{contaminant})) * C_{contaminant} \quad \text{(Eq. 4)}$$

Where $C1_{mixture\ 1}$ and $C2_{mixture\ 2}$ are the measured compositions of mixture 1 and mixture 2, $VF1_{uncontaminated\ oil}$ is the calculated volume fraction of uncontaminated oil for mixture 1, $VF2_{uncontaminated\ oil}$ is the calculated volume fraction of uncontaminated oil for mixture 2, $D_{uncontaminated\ oil}$ is the density of uncontaminated oil, $D_{contaminant}$ is the density of contaminant, $C_{uncontaminated\ oil}$ is the unknown composition of relatively pure uncontaminated oil and $C_{contaminant}$ is the unknown composition of relatively pure contaminant.

According to the Eqs. 3 and 4, there are only two unknowns for the two equations. The unknowns are the composition of the uncontaminated oil $C_{uncontaminated\ oil}$ and the composition of the $C_{contaminant}$. The unknown compositions can be solved for in a number of ways. For example, but not limited thereto, the two compositions may be computed using a matrix inversion operation.

Alternatively, or optionally as a check, the compositions may be computed using an iterative approach. Since the contaminant is largely degassed, the composition $C_{contaminant}$ can be initially assumed to be C6+. The results can be used to solve for the composition $C_{uncontaminated\ oil\ in\ the\ same\ mixture}$ (e.g., using a single equation, either Eq. 3 or Eq. 4). The results of $C_{uncontaminated\ oil}$ of one equation can be used to determine the composition $C_{contaminant}$ of the other equation. The composition $C_{contaminant}$ can be compared to the original assumption of C6+ and a difference computed.

Figure 8A:
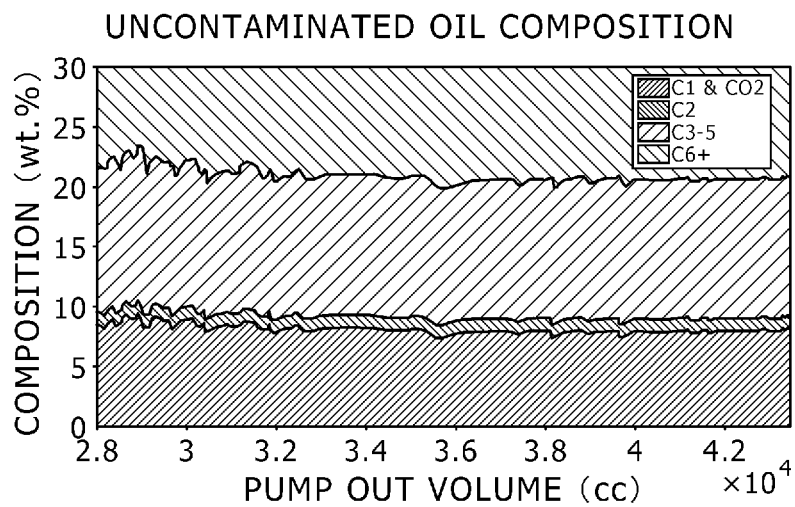
Figure 8B:
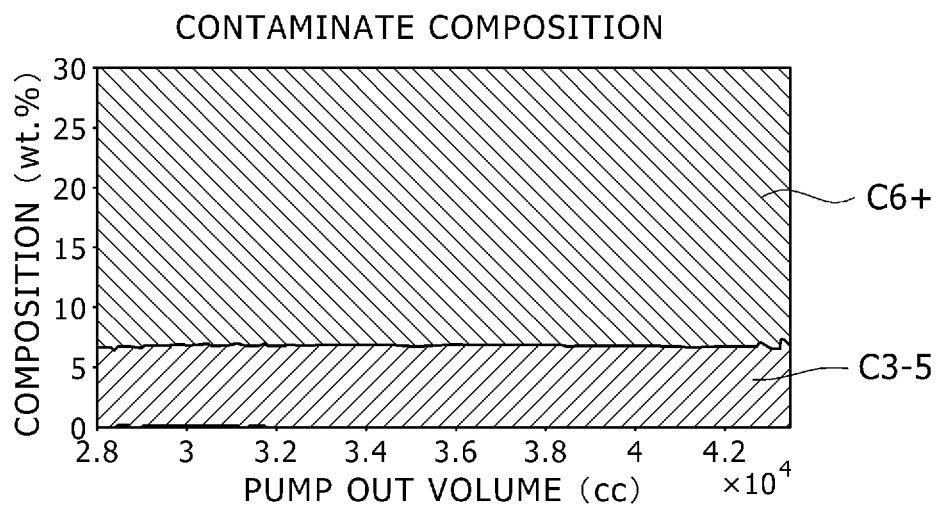

If the difference is above a certain threshold, the composition $C_{contaminant}$ of the other equation can be used for the first equation to compute a new composition $C_{uncontaminated}$ The process can repeat until the difference in compositions $C_{uncontaminated\ oil}$ or $C_{contaminant}$ fall below a minimum threshold indicating relative stability in the results. Turning now to exemplary figures FIG. 8A-8B, these graphs respectively show the computed uncontaminated oil composition and contaminant composition versus a pump out volume over time. The compositions are represented in terms of C1, C2, C3-5 and C6+, defined previously.

Figure 3A:
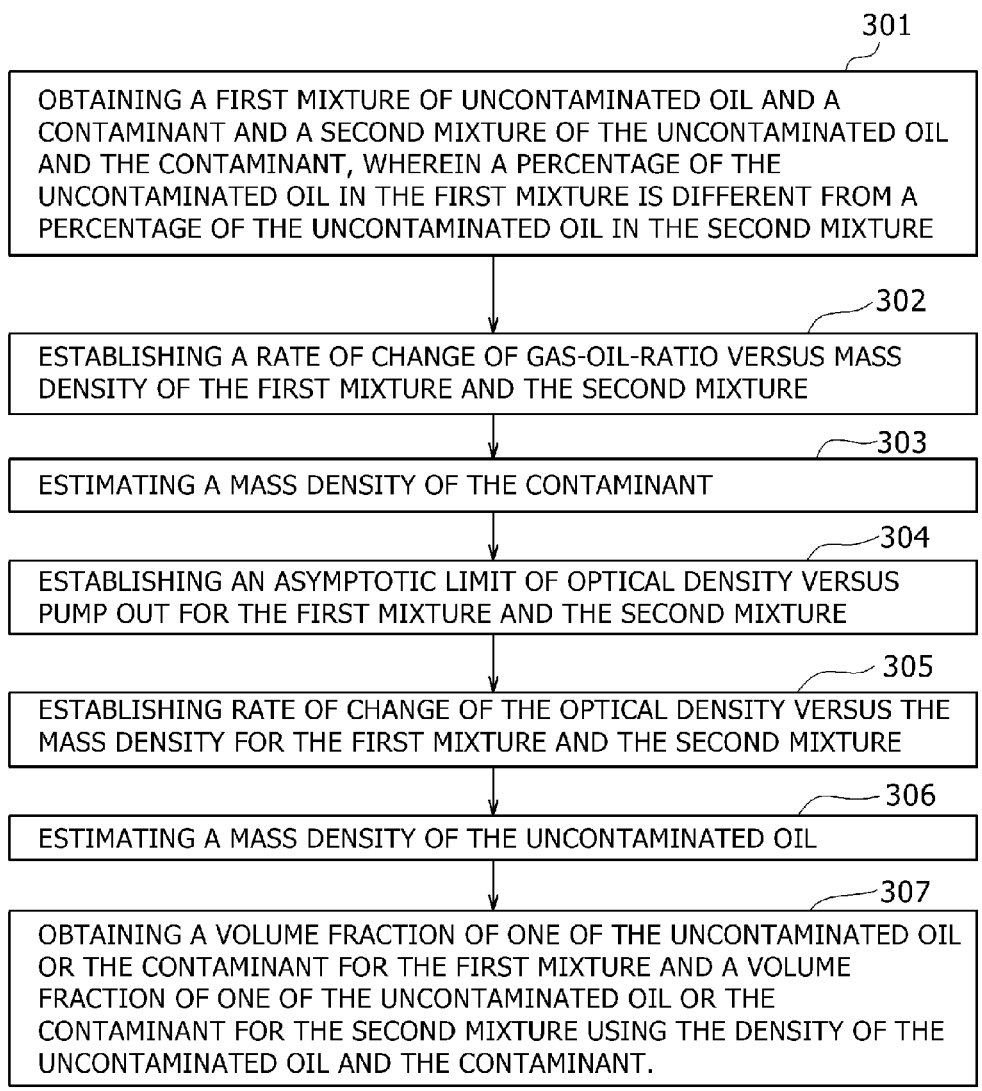
FIG. 3A depicts a flowchart of an estimation of volume fraction of uncontaminated oil or contaminant in accordance with an embodiment of the present disclosure.

Turning now to exemplary FIG. 3A, this figure comprises a flow chart of another embodiment of a method to compute the volume fraction of uncontaminated oil or contaminant. As shown in block 301, a first and second mixture of uncontaminated oil and contaminant are obtained. The first and second mixture may be obtained from a single flow line at different points in time or from two flow lines at different locations or configurations. The pumping rates used to obtain the first and second mixtures may be different and in some embodiments, one mixture may be obtained through a filter, membrane, or separator, among other methods. The percentage of uncontaminated oil in the first mixture is different than the percentage of uncontaminated oil in the second mixture. Similarly, the difference between the first mixture and the second mixture may be expressed using percentages of contaminant.

Referring generally to block 302, a rate of change is established for both mixtures with respect to gas-oil ratio (GOR) and mass density. The mass density of the first and the second mixture is established using standard techniques, such as a densitometer. Both the first and the second mixture are measured for GOR. As a result, a trend between the first and second mixture can be visualized and a best fit line plotted for the data points (see FIG. 4 for example). Using the best fit line and the assumption that the contaminant is largely degassed, the mass density of the contaminant can be estimated (e.g., block 303) from the intersection of the best fit line and approximately zero axis on the GOR scale.

Referring now to block 304, an optical device may be used to measure optical density (OD) against a pump out volume (see FIG. 5 for example). A best fit line plotted from data collected from the first and second mixture may show a second order asymptotic limit of OD as the pump out volume increases (assuming that percentages of uncontaminated oil increase with increasing pump out volume). Relatively pure uncontaminated oil should have the highest optical absorption of components in the first and second mixtures. Establishing a trend over time in which the first and second mixture reflect different percentages of uncontaminated oil or contaminant allows the visualization of an upper limit of OD as the percentage of uncontaminated oil increases. The asymptote reflecting this limit may be used to estimate OD of uncontaminated oil.

Exemplary block 305 refers to establishing a rate of change of the optical density versus the mass density for the first and second mixture (see FIG. 6 for example). As previously described, the optical density may be determined via an optical device, such as a spectrometer for example, and the mass density may be determined via a densitometer for example. A best fit line for the OD data and the mass density data allows extrapolation of the trend to an intersection with the estimated OD of uncontaminated oil. The intersection point with the extrapolated trend line indicates an estimate of mass density for the uncontaminated oil.

With the estimation of the mass density for the uncontaminated oil, Eqs. 1 and 2 can be used to calculate the volume fractions of the uncontaminated oil and the contaminant using the measured mass densities of the first and second mixtures, the estimated mass density of the uncontaminated oil, and the estimated mass density of the contaminant. The value in the first and second mixtures of the volume fraction for the uncontaminated oil and/or the volume fraction for the contaminant may be used to indicate the progress or effectiveness of well bore cleaning operations, or they may be used to estimate an appropriate time to take a downhole sample of fluid from the formation for further analysis. (see FIG. 7 for example).

Turning generally now to FIG. 3B, the flow chart from blocks 301 to 307 has been described with reference to the previous figure and will not be further detailed with regard to FIG. 3B. FIG. 3B makes use of equations Eq. 5 and Eq. 6, shown below:

$$C1_{mixture1} = WF1_{uncontaminatedoil} * C_{uncontaminatedoil} + (1 - WF1_{uncontaminatedoil}) * C_{contaminant} \quad (Eq. 5)$$

$$C2_{mixture2} = WF2_{uncontaminatedoil} * C_{uncontaminatedoil} + (1 - WF2_{uncontaminatedoil}) * C_{contaminant} \quad (Eq. 6)$$

In these equations, the composition of the contaminant and the composition of the uncontaminated oil can be determined using $C1_{mixture\ 1}$ and $C2_{mixture\ 2}$, the measured compositions of mixture 1 and mixture 2, the weight fraction of uncontaminated oil for the first mixture, $WF1_{uncontaminated\ oil}$, and the weight fraction of uncontaminated oil for the second mixture, $WF2_{uncontaminated\ oil}$. The weight fractions are determined from the volume fraction of uncontaminated oil for the first mixture, the volume fraction of uncontaminated oil for the second mixture, the density of the contaminant, and the density of the uncontaminated oil.

In order to solve for compositions of uncontaminated oil and contaminant, an optical device, such as a spectrometer for example, is used to determine the composition of the first mixture and the composition of the second mixture (as shown in block 308). Additionally, the volume fractions are converted to weight fractions, block 309. One exemplary way of converting the volume fraction of the uncontaminated oil to a weight fraction of the uncontaminated oil is to multiply the volume fraction of the uncontaminated oil by the density of the uncontaminated oil, and divide this figure by the sum total of the volume fraction of the uncontaminated oil multiplied by the density of the uncontaminated oil plus the volume fraction of the contaminant (or 1-volume fraction of the uncontaminated oil) multiplied by the density of the contaminant. The weight fraction of the contaminant may be determined by subtracting the weight fraction of the uncontaminated oil from 1.

Accordingly, the end result of both block 309 is four calculated variables, weight fraction 1 (e.g., representing mixture 1) of uncontaminated oil, weight fraction 1 of contaminant, weight fraction 2 (e.g., representing mixture 2) of uncontaminated oil, and weight fraction 2 of contaminant. Of course, weight fraction 1 of uncontaminated oil and weight fraction 1 of contaminant are related by the following equation, Eq. 7:

$$1 = WF1_{uncontaminatedoil} + WF1_{contaminant} \quad (Eq. 7)$$

Where $WF1_{uncontaminated\ oil}$ is the weight fraction 1 of uncontaminated oil and $WF1_{contaminant}$ is the weight fraction 1 of contaminant. This relationship holds true for the volume fractions as well as the weight fractions. Therefore, both weight fractions or volume fractions (e.g., $WF_{uncontaminated\ oil}$ and $WF_{contaminant}$ for example for a specific mixture of uncontaminated oil and contaminant), can be calculated after the determination of one directly computed weight fraction or volume fraction for that mixture.

With the weight fractions for uncontaminated oil and contaminant calculated, the only unknowns in Eqs. 5 and 6 are the composition of uncontaminated oil and the composition of contaminant. The unknown compositions can be solved for in a number of ways. For example, but not limited thereto, the two compositions may be computed using a matrix inversion operation.

Alternatively, or optionally as a check, the compositions may be computed using an iterative approach. Since the contaminant is largely degassed, the composition $C_{contaminant}$ can be initially assumed to be C6+. The results can be used to solve for the composition $C_{uncontaminated\ oil}$ in the same mixture (e.g., using a single equation, either Eq. 5 or Eq. 6). The results of $C_{uncontaminated\ oil}$ of one equation can be used to determine the composition $C_{contaminant}$ of the other equation. The composition $C_{contaminant}$ can be compared to the original assumption of C6+ and a difference computed.

If the difference is above a certain threshold, the composition $C_{contaminant}$ of the other equation can be used for the first equation to compute a new composition $C_{uncontaminated}$ The process can repeat until the difference in compositions $C_{uncontaminated\ oil}$ or $C_{contaminant}$ fall below a minimum threshold indicating relative stability in the results. Turning now to exemplary figures FIG. 8A-8B, these graphs respectively show the computed uncontaminated oil composition and contaminant composition versus a pump out volume over time. The compositions are represented in terms of C1, C2, C3-5 and C6+, defined previously.

The downhole in-situ process may be performed with a variety of embodiments of tools and components. For an exemplary and non-limiting description of two embodiments, refer generally to FIGS. 9A-9B. These figures generally represent schematic views of in-situ fluid analysis (IFA) components that may be used with either wire line, drilling, or other forms of conveyance.

Figure 9A:
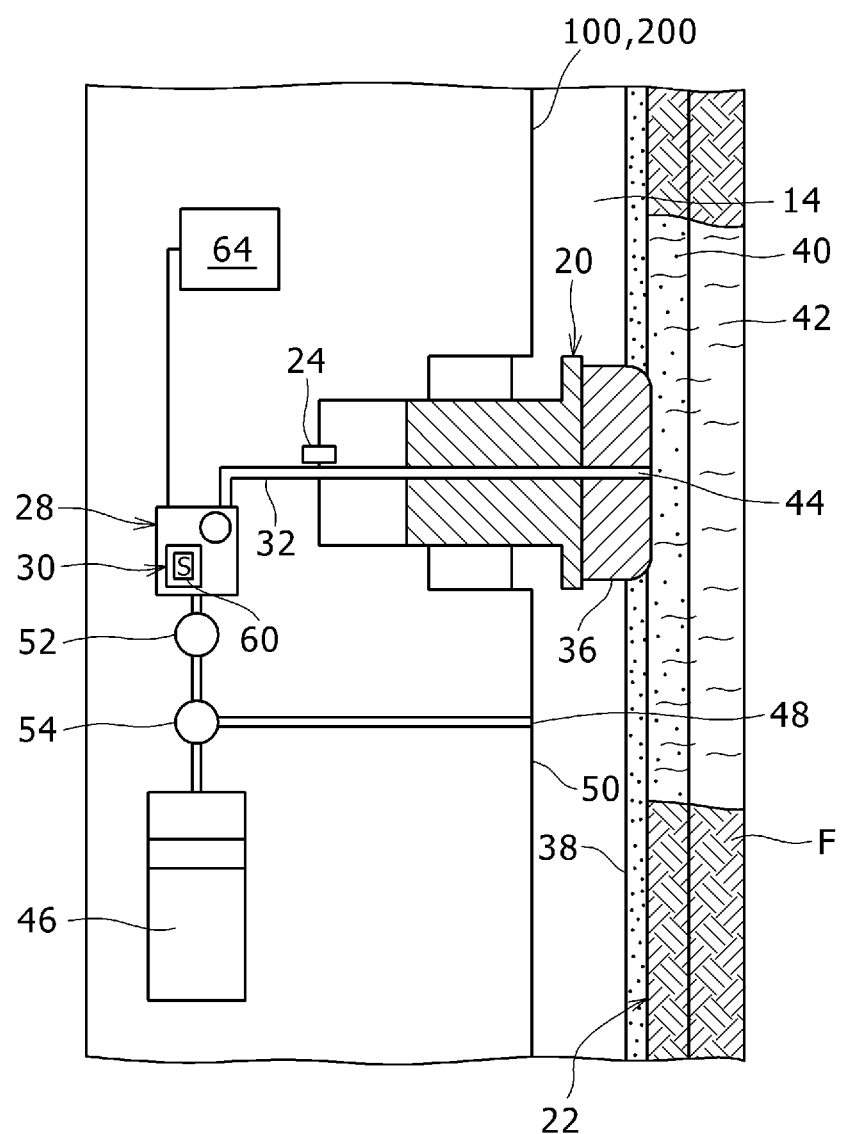
FIG. 9A depicts a schematic view of a portion of an apparatus for downhole fluid analyzer with a single fluid intake in accordance with an embodiment of the present disclosure.

Referring generally to FIG. 9A, this exemplary figure is a schematic view of a portion of a downhole tool 100, 200, portions, components or techniques of which may be reflected in embodiments of either of the exemplary downhole tools 100 and 200 shown in FIGS. 1A and 1B respectively, for example. The probe 20 may be extended from within the downhole tool 100, 200 for substantially coupling with a wellbore wall 22. In some cases, the probe is provided with a packer 36 to enhance with the wellbore wall 22. Packer 36 may contact the wellbore wall 22 and form a seal within the mud cake 38 lining the wellbore wall 22.

As shown, the contaminants, such as the mud cake 38, may seep into the wellbore wall 22 to create a permeated zone 40 about the wellbore 14. The permeated zone 40 may be contaminated by mud filtrate and other wellbore fluids that may affect the composition of the surrounding formations, such as formation F. A radially deeper section of uncontaminated oil 42 may be located within the formation F beyond the permeated zone 40.

By providing the fluid analyzer 30 in the downhole tool 100, 200, data may be collected in-situ at downhole conditions (e.g., at temperatures and pressure) where formation evaluation is performed. This allows for a more accurate assessment of the fluid mixture and fluid properties that exist down hole. Fluid samples may also be taken to a surface and/or offsite location, and analyzed in one or more fluid analyzers at those locations, in order to verify or determine specific properties and composition in more detail As shown, a single flow line 32 extends through the probe 20 and is fluidly coupled to the bore hole wall 22. Mixtures of uncontaminated oil 42 and contaminant 40 may enter into flow line 32 due to pressure differentials caused either naturally or artificially, such as via pumps, etc. Once within flow line 32, the mixtures of downhole fluid will proceed into the downhole tool 100, 200 and onto the formation evaluation tool 28. The formation evaluation tool 28 may then be used to analyze, test, sample and/or otherwise evaluate the mixture of downhole fluid.

A fluid analyzer 30 may be a part of the formation evaluation tool 28 and may be fluidly coupled to the flow line 32 for analyzing the mixtures of downhole fluid. In addition to the fluid analyzer 30, a densitometer 24 may be provided for measuring the density of mixtures in the flow line 32. In some cases, the density may be measured dynamically while the mixtures of downhole fluid continue to pass through the flow line 32.

In still other embodiments, a sample chamber 46 may also be coupled to the flow line 32 for receiving samples of the mixtures of downhole fluid. Mixtures of downhole fluid collected in the sample chamber 46 may be collected therein for retrieval and study at the surface. Uncollected samples of mixtures of downhole fluid may be exited through an outlet 48 in housing 50 of the downhole tool 100, 200.

Embodiments of the fluid analyzer 30 may include an optical device 60 with one or more sensors S to measure a property of the mixtures of downhole fluid and/or determine the composition of uncontaminated oil and contaminant. In some cases, optical density may be measured by the one or more sensors S. While in other cases, the optical device 60 may comprises a spectrometer able to optically determine composition of one or more mixtures of downhole fluid.

The sensor(s) S may also include but are not limited to, for example, gauges (e.g., quartz), densitometers, viscometers, resistivity sensors, nuclear sensors, and/or other measurement and/or detection devices capable of determining downhole data relating to, for example, downhole conditions and/or fluid properties. The fluid properties may comprise but are not limited to, for example, mass density, optical density, optical absorbance and gas-oil ratio (GOR). The fluid properties can be measured a plurality of times to generate in-situ measurement data at different times and concentrations of mixtures of downhole fluid.

Figure 9B:
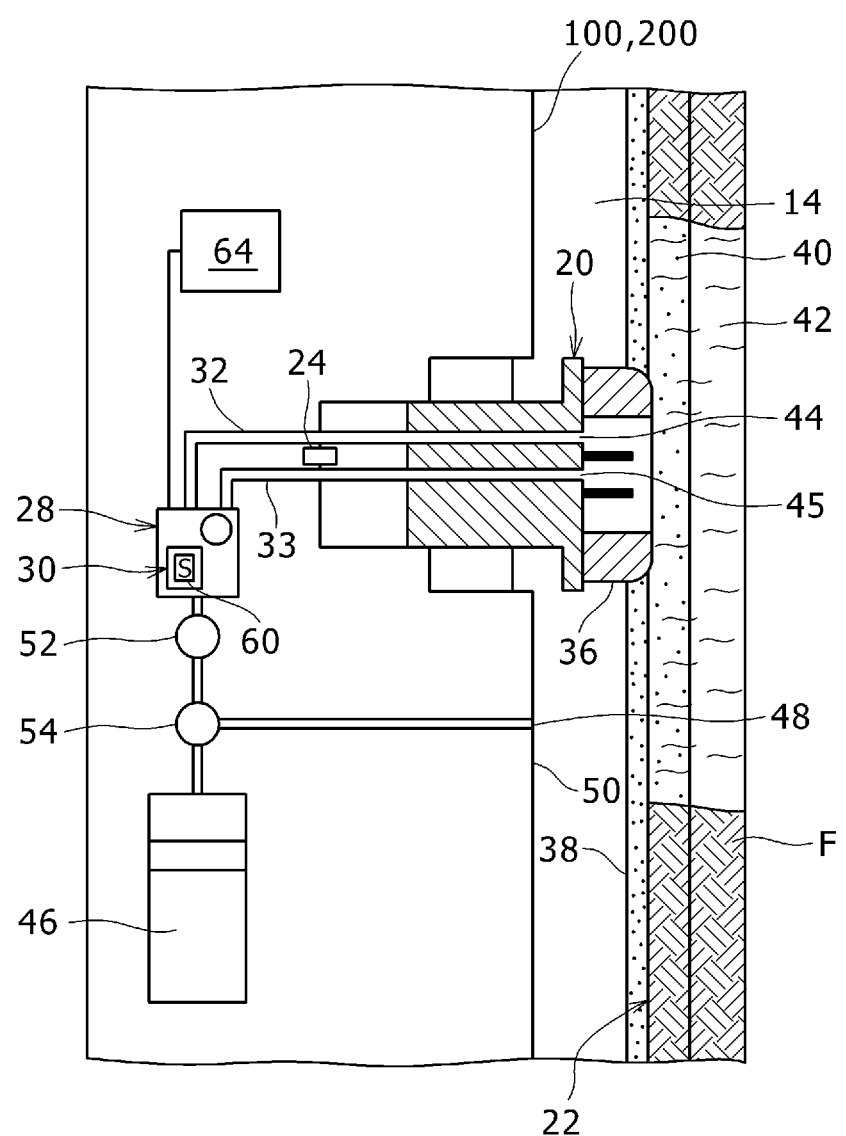
FIG. 9B depicts a schematic view of a portion of an apparatus for downhole fluid analyzer with a first and second fluid intake in accordance with a further embodiment of the present disclosure.

Referring generally now to exemplary FIG. 9B, this figure is a schematic view of a portion of another embodiment of downhole tool 100, 200. In the embodiment shown, a formation evaluation tool 28 may be provided with two flow lines, a first flow line 32 and a second flow line 33. In the probe 20, first flow line 32 and second flow line 33 may draw fluid into the downhole tool 100, 200 through first inlet 44 and second inlet 45, respectively.

Figure 10:
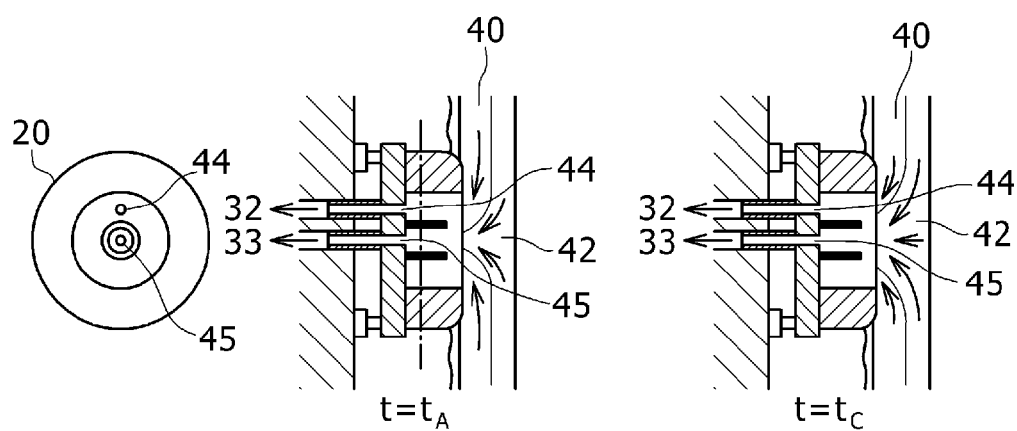
FIG. 10 depicts a schematic view of a first and second flow line fluid intake in which one fluid intake encompasses the other fluid intake in accordance with an embodiment of the present disclosure.

Turning briefly to FIG. 10, the first flow line 32 and the second flow line 33 may be fluidly coupled to first inlet 44 and second inlet 45, which in turn may be concentrically configured in some embodiments. Of course, the first inlet 44 and second inlet 45 do not have to be configured with one inlet concentrically surrounding another inlet, and instead may be addressing different locations of the same formation, for example.

As shown in FIG. 10, the second inlet 45, may be surrounded concentrically by the first inlet 44. In such a configuration, the second flow line 33, coupled to the second inlet 45, may obtain mixtures of downhole fluid that are relatively richer, or possess a higher percentage of uncontaminated oil over time than the first flow line 32. The second flow line 33, may further be used as a sample line from which a sample mixture of downhole fluid of relatively uncontaminated oil may be obtained as the cleaning process or sampling process progresses over time.

The first inlet 44 of the first flow line 32 may surround the second inlet 45 of the second flow line 33. The first flow line 32 may effectively guard the second flow line 33 from a higher percentage of contaminant, and therefore may be referred to as a guard line that obtains mixtures of downhole fluid that are richer in contaminant than second flow line 33.

This configuration may be utilized to obtain a relatively contaminant free sample for the second flow line 33. In some cases, this technique may be referred to as focused sampling. Relatively contaminant free mixtures of downhole fluid may be obtained due to various operation methods. For example, a configuration of the first inlet 44 may have a larger area open to a sandface and can therefore pump fluids at a higher rate and accelerate the flow of the contaminants into the first flow line 32. The second inlet 45 may consequently pump at a more moderate rate, thereby resulting in a mixture of downhole fluids with a higher percentage of uncontaminated oil. Visually, this scenario is represented in the second figure of FIG. 10, when time t is equal to $t_C$ (time $t_C$>time $t_A$). In other operation schemes, starting the pump for the second flow line 33 may be delayed until after the pump for the first flow line 32 has been operating for a while. In some cases, filters may be placed at the end of flow lines either in this configuration or others, in order to control or reduce the inflow of contaminants.

As the pumps for the first inlet 44 and the second inlet 45 continue to operate, the flow of contaminant 40 is primarily directed to the first inlet 44 surrounding the second inlet 45 and the flow of uncontaminated oil 42 is primarily directed to the second inlet 45. Even though one probe 20 with a first inlet 44 and a second inlet 45 is depicted, one or more probes, dual packers and related inlets may be provided to receive downhole fluids and pass them to first flow line 32 and second flow line 33 or to other embodiments and configurations of flow lines. Examples of downhole tools and fluid communication devices, such as probes, that may be used are depicted in U.S. Pat. No. 7,458,252, incorporated by reference herein. In addition, examples of the focused sampling configuration shown in FIG. 10 are also depicted in U.S. Patents and Publications, No. U.S. Pat. No. 6,956,204, U.S. Pat. No. 8,024,125, US20050182566, US20140193153 and US20140180591, which all are incorporated by reference herein.

As stated in previously, some embodiments may comprise a spectrometer 60 including a light source and filters. In some cases, the light from the light source goes into channels of the spectrometer via fiber optics bundles. The light source may be a halogen lump or a Light Emitting Diode (LED), among others. The spectrometer may have a plurality of filter elements, each of which may correspond to a different band of wavelengths used for determining different compositional components. In other cases, the optical device may be used to jointly or relatively simultaneously measure the first flow line 32 and the second flow line 33.

Referring back to FIG. 9B again, in some embodiments, the flow of the mixtures of downhole fluid into and/or through the downhole tool 100, 200 may be controlled by one or more flow control devices, such as a pump 52, a sample chamber 46, valves 54 and/or other devices. Optionally, a downhole unit 64 may be provided to communicate with the formation evaluation tool 28, the fluid analyzer 30, and/or other portions of the downhole tool 100, 200 for the passage of signals (e.g., data, power, command, etc.) there between. Downhole unit 64 may also be configured to communicate with surface unit 34 to enable communications between downhole tool 100, 200 and the surface. Optionally, one or more flow lines may also be provided in the tool for calibration of the fluid analyzer.

Some embodiments according to this disclosure may estimate not only the level of contamination in a first flow line and a second flow line, but also a composition of the uncontaminated oil and contaminant that flow in the first flow line and the second flow line in mixtures in various proportions. According to one embodiment of this disclosure, in addition to a reduction of uncertainty with regards to contamination estimation, estimation of composition on a relatively instantaneous basis may be obtained.

The preceding description has been presented only to illustrate and describe certain embodiments. It is not intended to be exhaustive or to limit the disclosures to any precise form disclosed. Many modifications and variations are possible in light of the above teaching. The embodiments and aspects were chosen and described in order to best explain principles of the disclosures and its practical applications. The preceding description is intended to enable others skilled in the art to best utilize the principles in various embodiments and aspects and with various modifications as are suited to the particular use contemplated. It is intended that the scope of the disclosures be defined by the following claims.

What is claimed is:

1. A method for analyzing well properties in-situ comprising:
    (a) obtaining a first mixture of uncontaminated oil and a contaminant and a second mixture of the uncontaminated oil and the contaminant, wherein a percentage of the uncontaminated oil in the first mixture is different from a percentage of the uncontaminated oil in the second mixture;
    (b) establishing one or more rates of change of a physical property of the first mixture and the second mixture to estimate a mass density of the uncontaminated oil and a mass density of the contaminant, wherein the one or more rates of change of a physical property of the first mixture and the second mixture comprises a rate of change of a gas-oil-ratio of the first mixture and a gas-oil ratio of the second mixture versus a mass density of the first mixture and a mass density of the second mixture in order to estimate the mass density of the contaminant, and a rate of change of an optical density of the first mixture and an optical density of the second mixture versus a pump out volume for the first mixture and a pump out volume for the second mixture to be used in estimating the mass density of the uncontaminated oil, based on an asymptotic limit of optical density versus pump out for the first mixture and the second mixture; and
    (c) obtaining a volume fraction of one of the uncontaminated oil or the contaminant for the first mixture and a volume fraction of one of the uncontaminated oil or the contaminant for the second mixture using the mass density of the uncontaminated oil and the mass density of the contaminant and the mass density of the first mixture and the mass density of the second mixture.

2. The method according to claim 1, wherein the volume fraction of one of the uncontaminated oil or the contaminant is communicated to a surface unit to indicate a status of a well service operation.

3. The method according to claim 1, wherein one or more rates of change of a physical property of the first mixture and the second mixture comprises a rate of change of the optical density of the first mixture and the optical density of the second mixture versus the mass density of the first mixture and the mass density of the second mixture; and
    wherein the rate of change of the optical density of the first mixture and the optical density of the second mixture versus the pump out volume for the first mixture and the pump out volume of the second mixture is used in addition to the rate of change of the optical density of the first mixture and the optical density of the second mixture versus the mass density of the first mixture and the mass density of the second mixture in order to estimate the mass density of the uncontaminated oil.

4. The method according to claim 1, wherein the method further comprises:
    (d) using an optical device to determine a composition of the first mixture and a composition of the second mixture; and
    (e) determining a composition of the contaminant and a composition of the uncontaminated oil using the composition of the first mixture, the composition of the second mixture, the volume fraction of one of the uncontaminated oil or contaminant for the first mixture, the volume fraction of one of the uncontaminated oil or contaminant for the second mixture, and the mass density of the uncontaminated oil or the mass density of the contaminant.

5. The method according to claim 4, wherein the composition of the uncontaminated oil is communicated to a surface unit.

6. The method according to claim 1, wherein the first mixture is obtained from a first flow line and the second mixture is obtained from a second flow line.

7. The method according to claim 1, wherein the first mixture and the second mixture are obtained from a single flow line at different times.

8. A method for determining well properties in-situ, comprising:
    (a) obtaining a first mixture of uncontaminated oil and a contaminant and a second mixture of the uncontaminated oil and the contaminant, wherein a percentage of the uncontaminated oil in the first mixture is different from a percentage of the uncontaminated oil in the second mixture;
    (b) establishing a rate of change of gas-oil-ratio versus mass density of the first mixture and the second mixture;
    (c) estimating a mass density of the contaminant;
    (d) establishing an asymptotic limit of optical density versus pump out for the first mixture and the second mixture;
    (e) establishing rate of change of the optical density versus the mass density for the first mixture and the second mixture;
    (f) estimating a mass density of the uncontaminated oil based on the asymptotic limit and the rate of change of the optical density versus the mass density; and
    (g) obtaining a volume fraction of one of the uncontaminated oil or the contaminant for the first mixture and a volume fraction of one of the uncontaminated oil or the contaminant for the second mixture using the density of the uncontaminated oil and the contaminant and the mass density for the first mixture and the mass density for the second mixture.

9. The method of claim 8, wherein the volume fraction one of the uncontaminated oil or the contaminant for the first mixture or the second mixture is communicated to a surface unit.

10. The method of claim 9, wherein the optical device is a spectrometer.

11. The method of claim 8, further comprising:
    (h) using an optical device to determine a composition of the first mixture and a composition of the second mixture;
    (i) converting the volume fraction of the one of the uncontaminated oil or the contaminant for the first mixture and the volume fraction of the one of the uncontaminated oil or the contaminant for the second mixture into a weight fraction of the first mixture and a weight fraction of the second mixture; and (j) determining a composition of the uncontaminated oil and a composition of the contaminant using the composition of the first mixture, the composition of the second mixture, the weight fraction of the first mixture and the weight fraction of the second mixture.

12. The method according to claim 8, wherein the first mixture is obtained from a first flow line and the second mixture is obtained from a second flow line.

13. The method according to claim 8, wherein the first mixture and the second mixture are obtained from a single flow line at different times.

14. A downhole fluid analyzer comprising:
a probe having one or more flow lines for obtaining a first mixture of uncontaminated oil and a contaminant and a second mixture of the uncontaminated oil and the contaminant, wherein a percentage of the uncontaminated oil in the first mixture is different from a percentage of the uncontaminated oil in the second mixture, wherein the one or more flow lines are a first flow line and a second flow line encompassed by the first flow line;
an optical device for determining a first optical density of the first mixture and a second optical density of the second mixture for determining a composition of the first mixture and a composition of the second mixture;
a densitometer for determining a first density of the first mixture and a second density of the second mixture;
a processor to estimate a density of the contaminant and to estimate a density of the uncontaminated oil; and
wherein the processor determines a volume fraction of one of the uncontaminated oil or contaminant for the first mixture and a volume fraction of one of the uncontaminated oil or contaminant for the second mixture using the density of the uncontaminated oil and the density of the contaminant and the first density of the first mixture and the second density of the second mixture.

15. The downhole fluid analyzer of claim 14, further comprising a downhole unit to communicate with a surface unit;
wherein the volume fraction of one of the uncontaminated oil or the contaminant of one of the first mixture or the second mixture is communicated to the surface unit.

16. The downhole fluid analyzer of claim 14, wherein the processor further computes a composition of the uncontaminated oil and a composition of the contaminant from the volume fraction of one of the uncontaminated oil or contaminant for the first mixture, the volume fraction of one of the uncontaminated oil or contaminant for the second mixture, the mass density of the uncontaminated oil or the mass density of the contaminant, and the composition of the first mixture and the composition of the second mixture.

\* \* \* \* \*